United States Patent [19]

Schorr

[11] 4,383,535

[45] May 17, 1983

[54] METHOD FOR PREVENTING REMANENCE PHENOMENA FROM INTERFERING WITH MAGNETIC FIELD SENSING SYSTEMS AND A DEVICE FOR IMPLEMENTATION OF THE METHOD

[75] Inventor: Wolfgang Schorr, Heppenheim, Fed. Rep. of Germany

[73] Assignee: Siemens Aktiengesellschaft, Berlin & Munich, Fed. Rep. of Germany

[21] Appl. No.: 197,645

[22] Filed: Oct. 16, 1980

[30] Foreign Application Priority Data

Nov. 3, 1979 [DE] Fed. Rep. of Germany ....... 2944490

[51] Int. Cl.³ ............................................. A61B 5/10
[52] U.S. Cl. .................................... 128/777; 307/101
[58] Field of Search ............... 128/777; 307/101, 309; 433/68, 69; 324/251

[56] References Cited

U.S. PATENT DOCUMENTS

| | | | |
|---|---|---|---|
| 3,482,163 | 11/1969 | Dierker et al. | 324/251 X |
| 3,772,617 | 11/1973 | Ciesielka | 307/101 X |
| 4,059,798 | 12/1977 | Peek et al. | 324/251 X |
| 4,303,077 | 12/1981 | Lewin et al. | 128/777 |

Primary Examiner—Kyle L. Howell
Assistant Examiner—John C. Hanley
Attorney, Agent, or Firm—Hill, Van Santen, Steadman, Chiara & Simpson

[57] ABSTRACT

In an exemplary embodiment, one or more flux pickups with ferromagnetic properties, preferably Hall generators provided with antennas, are provided for the detection of a field flux or of a change of field flux proceeding from a field generator. Magnetization pulses ($I_2$) are provided in periodic sequence to the flux pickups (I through VIII), the pulse height and width ($t_{im}$) being selected in such manner that the saturation field strength ($M_s$) of the flux pickups is therewith achieved, so as to produce a maximum residual magnetization ($M_R$). The flux pickups (I through VIII) are preferably driven by means of pulse-shaped signals ($I_1$), with the magnetization pulses being supplied in the pulse interval ($i_s$) of these signals synchronous to the pulse repetition rate. The method is particularly employed in gnathography for recording the lower jaw movement of a human being.

7 Claims, 4 Drawing Figures

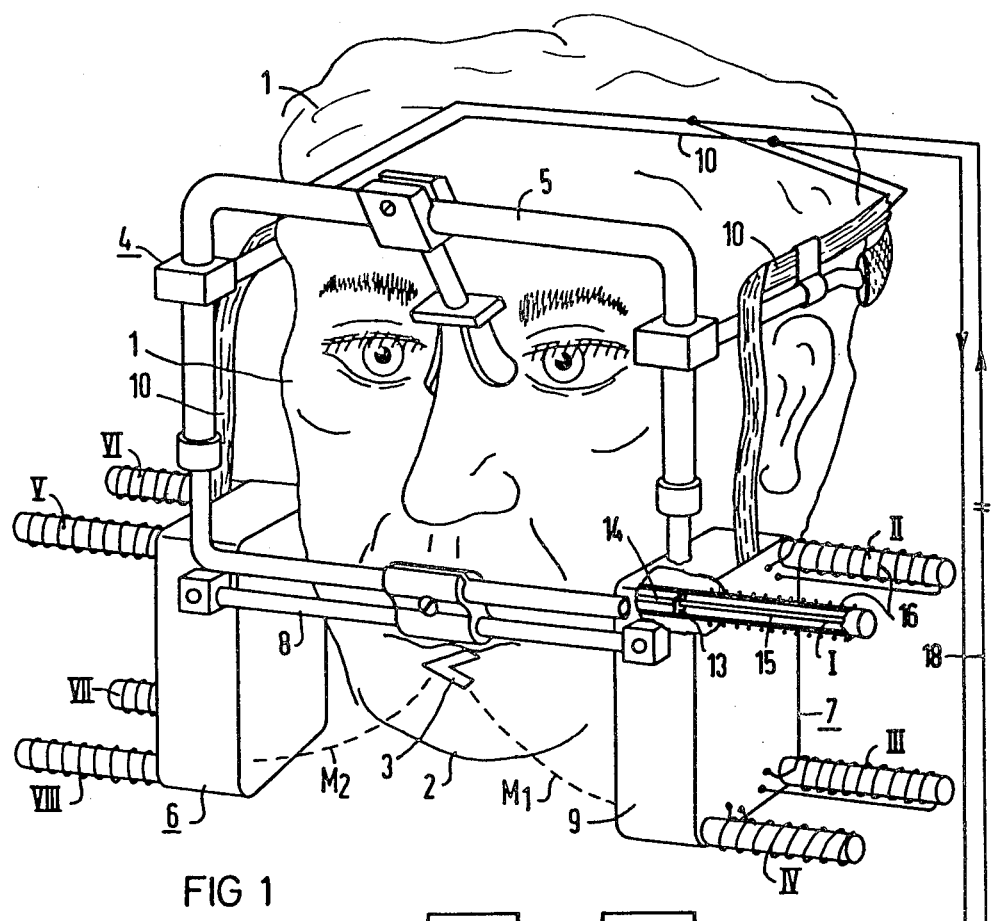
FIG 1
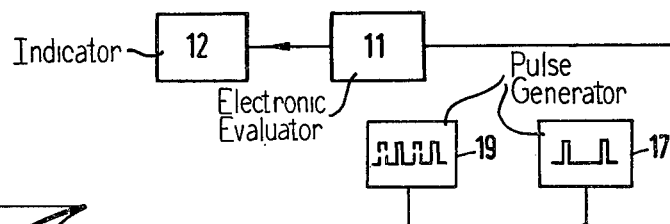
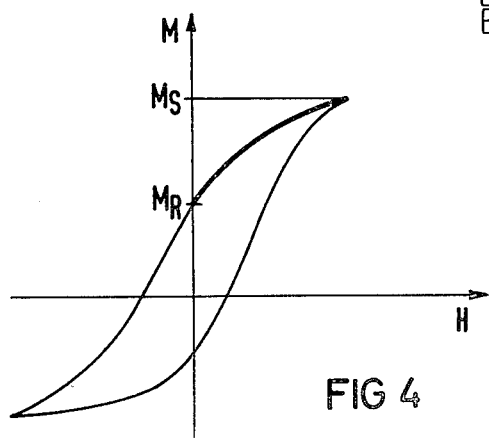
FIG 4

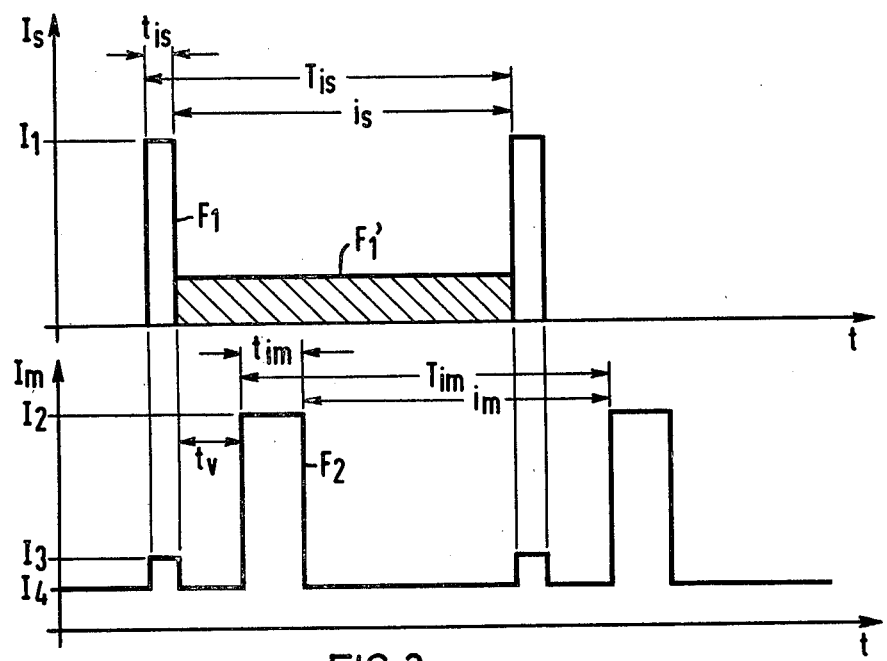
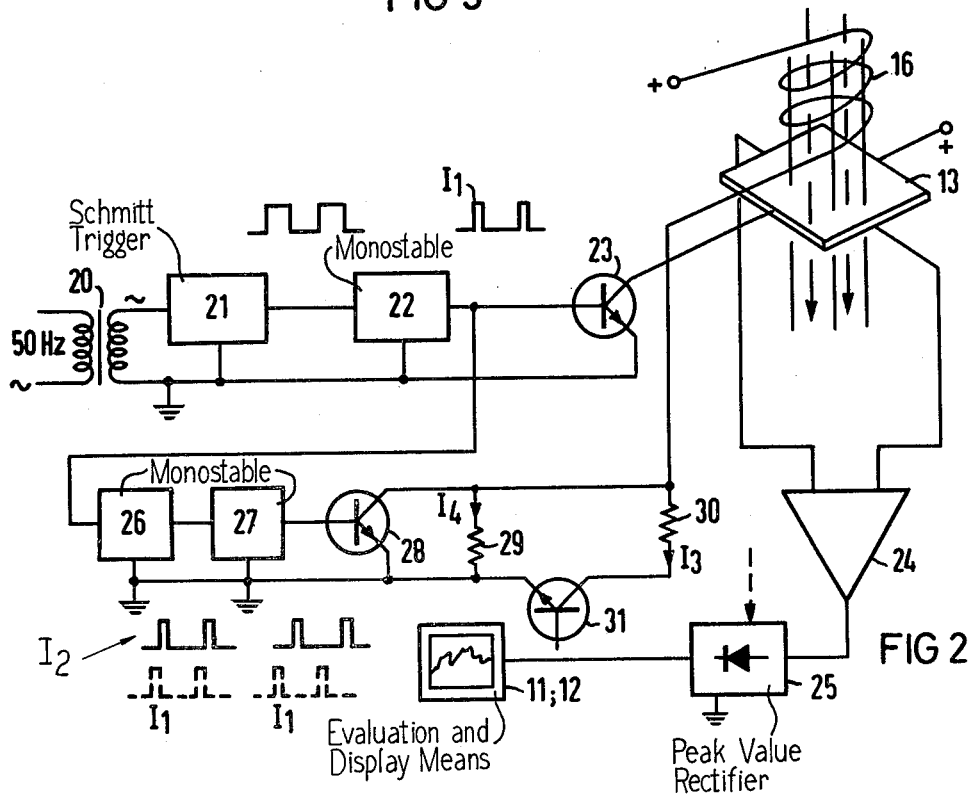

METHOD FOR PREVENTING REMANENCE PHENOMENA FROM INTERFERING WITH MAGNETIC FIELD SENSING SYSTEMS AND A DEVICE FOR IMPLEMENTATION OF THE METHOD

BACKGROUND OF THE INVENTION

The invention relates to a method for the elimination of remanence phenomena in reception systems and a device for the implementation of the method, in which flux pickups with ferromagnetic properties, preferably Hall generators provided with antennas, are provided for the detection of a field flux or, respectively, of a change of field flux proceeding from a field generator.

In reception systems in which, in particular, relatively small field changes are to be detected with the assistance of flux pickups such as Hall generators, and in which reproducible measuring results are to be achieved with signals gained from a change of field flux, no disruptive remanence phenomena having a negative influence on the evaluation of the signals should occur. Such disruptive remanence phenomena, however, occur due to the not absolutely remanence-free ferromagnetic materials of the flux pickups (Hall generators and, under certain conditions, antennas coupled thereto) given field changes, for example, given a change of location of the reception system in the earth's magnetic field or given approach of a measuring instrument with a further field generator.

An example of employment can be seen in gnathology, where one wishes to detect and record the motion of the lower jaw of a person with the assistance of a measuring device. The proposed measuring method provides that a magnetic field generator, for example a permanent magnet, be secured to the lower jaw of a patient and, at a distance from the magnetic field generator, a flux pickup system with Hall generators and antennas be arranged on the head of the patient. The field changes occurring given a motion of the lower jaw are detected by the pickup system in all three planes of motion and are evaluated via an electronic evaluation means. The structure of such a device is described in the German patent application P No. 28 42 764.2 or, respectively, P No. 28 14 551.9, and in the corresponding U.S. Applications Ser. No. 025,263 filed Mar. 29, 1979, and Ser. No. 100,146 filed Dec. 4, 1979 now U.S. Pat. No. 4,303,077 issued Dec. 1, 1981.

In order, in particular, to obtain clear and reproducible measuring results given such measuring devices, it is necessary that no disruptive remanence phenomena changing the initial point (zero point) of the measuring system occur.

Since, however, practically no absolutely remanence-free ferromagnetic materials exist for the flux pickups (Hall generators and antennas) and the earth's magnetic field also has a disruptive effect on the measuring operation, one must strive to eliminate the influence of the remanence.

A conceivable way to eliminate these disruptive remanence phenomena would be a demagnetization of the flux pickups. Such a way is revealed in the publication "Kuhrt/Lippmann, Hallgeneratoren", Springer-Verlag 1968, pages 32, 33. The method for this is to allow a magnetic alternating field with an amplitude $H > H_s$ to influence the ferromagnetic material and to then gradually decrease the amplitude of this alternating field. The magnetization thus circles the coordinate origin in hysteresis loops which become smaller and smaller and finally, given a disappearing alternating field amplitude, achieves the point $H = 0$, $M = 0$.

No external field can have an influence given this demagnetization method, which involves a relatively great expenditure of time. A precise demagnetization, thus, is only possible in a field-free space. In order to avoid the earth's magnetic field, a demagnetization is accordingly only possible perpendicular to the earth's magnetic field and without a measuring magnet. This method, thus, is not suitable for many use cases.

SUMMARY OF THE INVENTION

The object of the present invention is to specify a method and a device for implementation of the method which are improved with respect thereto, which functions independently of the existing earth's magnetic field and other, potentially disruptive field influences such as, for example, a measuring magnet or the like, and with which clear and reproducible measuring results can be achieved.

This object is achieved by means of the invention in that magnetization pulses are supplied to the flux pickups in periodic sequence, the pulse height and width being selected in such manner that the saturation field strength of the flux pickups is therewith achieved. The flux pickups are preferably driven by means of pulse-shaped signals, whereby the magnetization pulse is supplied in the pulse interval of these signals synchronous to the pulse repetition rate. By means of charging the pickup system with magnetization pulses formed by means of short d.c. pulses of specific pulse magnitude in the pulse intervals, as proposed, it is guaranteed that the output voltage at the flux pickup (Hall generator) is subject to uniform initial conditions. Since the intermediate pulse is repeated after each measuring pulse with which the flux pickup is driven, uniform initial conditions are thus always created. After the end of the pulse, the magnetization returns to the value $M_R$ which represents the maximum possible remanence of the material employed for the flux pickup. This value is independent of any outside fields which may potentially occur.

Advantageous further developments and embodiments of the invention are contained in the subclaims. The method is explained in greater detail on the basis of the Figures of the accompanying sheets of drawings and a device for implementing the method is revealed. Other objects, features and advantages will be apparent from this detailed disclosure and from the appended claims.

BRIEF DESCRIPTION OF THE DRAWINGS

FIG. 1 is a diagrammatic perspective view showing a device for detecting the motion of the lower jaw of a patient;

FIG. 2 is a basic circuit diagram for the drive, on the one hand, of a Hall generator with pulse-shaped signals and, on the other hand, of a magnetization coil with pulses which are chronologically offset with respect thereto;

FIG. 3 is a pulse diagram showing operation according to the inventive method; and FIG. 4 is a hysteresis loop of a ferromagnetic material.

DETAILED DESCRIPTION

In a diagrammatic presentation, FIG. 1 shows a device for determining the location, the attitude, and/or a change of location or attitude of a point of the lower jaw of a patient. In the Figure, 1 indicates the head of a patient and 2 indicates his lower jaw. A permanent magnet serving as the field generator is referenced with 3, being intra-orally secured in the oral cavity of the patient at a desired location of the lower jaw by means of suitable adhesive or bonding agents. The magnetic field generator 3 consists of two identically dimensioned bar magnets as are more closely described in the German patent application P No. 27 15 106. The magnetic field generator 3 generates two irregular, nonrotational symmetrical magnetic fields $M_1$, $M_2$ indicated in the Figure with broken lines.

A magnetic flux pickup arrangement 4 is situated extra-orally of the patient's mouth, said arrangement essentially consisting of a frame 5 supported on the head of the patient 1 and of a pickup system with pickup blocks 6 and 7 situated to the left and to the right of the lower jaw. The frame 5 is designed in a known manner as a combined spectacle or head frame and contains a plurality of joints (not referenced in greater detail) for adapting it to the varying head characteristics of the patient. The pickup blocks 6 and 7 are rigidly connected to one another by means of a rod 8 connected to the frame 5.

Each of the pickup blocks 6, 7 contains four magnetic flux pickups I through VIII which are mounted in a synthetic housing 9, namely, in such manner that they respectively lie parallel to one another. The signals picked up by the magnetic flux pickups I through VIII to be described in greater detail below, are supplied via multi-conductor lines 10 to an electronic evaluation means 11 and are supplied from there to a suitable indicator device 12.

The magnetic flux pickup I is partially illustrated in section in order to explain the structure of the magnetic flux pickups I through VIII. The magnetic flux pickup contains a lamellar Hall generator 13 serving as the sensor, antenna rods 14 and 15 of mumetal of different lengths lying against the effective surface of said Hall generator at both sides. When the lower jaw is moved, the field flux detected by the Hall generators 13 changes. The signals thereby generated by the Hall generators are supplied via a preamplifier (not illustrated in the Figure) arranged in the housing 9 to the electronics unit 11, where the signals are then processed for a visual display.

An induction coil 16 is wound in a single layer around each magnetic flux pickup. The single layer winding of the flux pickup has the advantage that, on the one hand, a good thermal dissipation is given and, on the other hand, a better magnetic field is generated for the magnetization. The four coils 16 of each block (6, 7) are connected in series and are connected in parallel to the four others of the other block. As shall be described in greater detail below, the coils 16 are supplied with periodic rectangular pulses by a pulse generator 19 via one conductive path of a double line 18. Reference numeral 17 indicates a further pulse generator which drives the Hall generators 13 with pulse-shaped signals via the other conductive path of the double line 18.

On the basis of a block diagram, FIG. 2 shows a control circuit for the Hall generators 13 which is particularly advantageous for very small field strengths, as well as a circuit diagram for driving the coils 16 with pulses.

A.C. signals with the mains frequency of fifty or sixty hertz, e.g. 50 Hz are supplied via an A.C. transformer 20, said signals being first supplied to a Schmitt trigger 21 for pulse shaping. A monostable flip-flop 22 then supplies drive pulses $I_1$ in a specific mark-to-space ratio, said drive pulses $I_1$ being subsequently supplied via a transistor 23 to the Hall generator 13.

The pulse signals attainable by means of the circuit revealed now provide information concerning the magnitude and waveshape (envelope) of the useful signal which is received from the Hall generators 13. In order to convert the pulses into a useful signal, these are first supplied via an amplifier 24 to a peak value rectifier 25. The signals obtained therefrom can then be evaluated and optically displayed with the assistance of a suitable evaluation (computer) and indicator means 11, 12.

The pulses generated by the clock generator 17 and, for example, with the assistance of the circuit arrangement according to FIG. 2 are referenced with $I_1$ in the pulse diagram according to FIG. 3. In the use case, the pulse width $t_{is}$ amounts to approximately 0.5 ms given a pulse period $T_{is}$ of 20 ms. The mark-to-space ratio (pulse width to pulse interval) $t_{is}/i_s$ is selected in the present case in such manner that the allowed effective driving power of the Hall generator is not exceeded, i.e., the area referenced with $F_1$ dare not be greater than the area referenced with $F_1'$ which corresponds to the driving power of the Hall generator given direct current (D.C.) excitation. The more extreme the mark-to-space ratio is, i.e. the shorter the pulses and the longer the pulse pauses are selected, the higher the maximum amplitude of the control current can be set and, thus, the more the sensitivity of the Hall generator can be increased.

In the pulse interval $i_s$, i.e. in the pulse pauses, short D.C. pulses $I_2$ are periodically supplied to the coils 16 with the assistance of the pulse generator 19. A circuit diagram for generating these pulses is revealed in FIG. 2. The drive pulses $I_1$ for the Hall generators 13 are supplied to a monostable flip-flop 26, a further monostable flip-flop 26 being driven with their trailing pulse edges. The flip-flop 26 determines the delay time, referenced in the pulse diagram according to FIG. 3 with $t_V$, with respect to the drive pulse $I_1$; the flip-flop 27 determines the pulse width with which the transistor referenced in the circuit diagram according to FIG. 2 with 28 and, thus, the magnetization coils 16 are driven. The pulses $I_2$ are supplied synchronous to the drive pulses $I_1$, with a frequency of 50 Hz in the present case. The point in time at which the pulses $I_2$ are supplied can, of and for itself, be randomly selected; it need only lie within the pulse pause $i_s$. Pulse height and pulse width are to be selected great enough that the saturation field strength for the flux pickups (Hall generator and antenna) is achieved with the magnetization pulses induced by the coils 16. The magnetization of the antenna system thereby achieves its saturation value $M_S$, in accord with the illustration of FIG. 4, which shows a hysteresis curve of a ferromagnetic material. The saturation field strength of the material provided for the pickups can thus always be achieved by means of the D.C. pulse $I_2$ periodically supplied in the pulse interval $i_s$. After the end of the pulse, the magnetization returns to the value $M_R$. This value, since it represents the maximum possible remanence for the system, is independent of any outside fields which may potentially occur. Since a repetition of the operation ensues after each measuring pulse, i.e., every twenty milliseconds (20 ms) in the exemplary embodiment, it is guaranteed that the output voltage at the Hall generators 13 is always subject to the same initial conditions.

The inventive method can also be employed given a non-pulsed control current. Given uniform control current, the magnetization pulses are supplied in periodic sequence to a desired location, whereby the control current or the measuring voltage is then blanked out during the duration of the magnetization pulses.

The coils 16 on each flux pickup I through VIII are geometrically identical, i.e., they have the same number of winding turns, the same diameters and lengths. If, during the measuring time $t_{is}$, a further, short D.C. pulse $I_3$ of specific size is connected to all pickups, as is revealed in the pulse diagram according to FIG. 3, then respectively identical magnetic fields are generated at the Hall generators 16. With the assistance of matching amplifiers provided for this purpose, the Hall generators can thus be balanced to the same sensitivity. By means of this feature, a simplified balance and an easier control of the balance can be achieved. The D.C. pulses $I_3$ arise by means of parallel connection of a resistor 30 via a transistor 31 to the transistor 28. The direct (D.C.) current $I_3$ is not present during a measurement.

In order to avoid the so-called "reversal error" in a field reversal (cf. publication Kuhrt/Lippmann, Pages 143/144), it is proposed in an advantageous development of the invention for the balance of the device or, respectively, for checking the balance, that the coils 16 be loaded with direct (D.C.) currents of equal magnitude and polarity ($I_4$ in FIG. 3) by means of the parallel connection of a resistor 29 to the transistor 28. A so-called offset voltage is generated at the amplifier outputs in this manner—upon condition that these were balanced to "zero" in the field-free state. If one selects the current strength, which corresponds to the field strength of each individual coil, high enough that it is greater than the sum of the field strength of the earth's magnetic field and the magnetic field, at no time will a field reversal and, thus, a reversal error occur at the Hall generator.

It will be apparent that many modifications and variations may be effected without departing from the scope of the novel concepts and teachings of the present invention.

I claim as my invention:

1. Method for preventing disruptive remanence phenomena in reception systems in which a plurality flux pickups with ferromagnetic properties are provided for the detection of a field flux and of a change of field flux proceeding from a field generator, comprising the steps of:

supplying a magnetization pulse to each flux pickup, said pulse having a characteristic such that the pulse height and width cause saturation of each flux pickup;

measuring the field flux from the field generator with each flux pickup after the magnetization step, and during a period when the remanence of each pickup due to said saturation is at a maximum.

2. Method according to claim 1, characterized in that the flux pickups (I through VIII) are Hall generators provided with ferromagnetic antennas, the magnetization step resulting in the saturation of the ferromagnetic antennas of the Hall generators;

the measuring of the field flux from the field generator which is coupled with each Hall generator, after the saturation of the ferromagnetic antennas by the magnetization step, being effected by supplying a control pulse ($I_1$) of electric current through each Hall generator, with the control pulses ($I_1$) being supplied periodically to each Hall generator and having a pulse interval ($i_s$) between the successive control pulses ($I_1$); and the magnetization step comprising supplying each magnetization pulse ($I_2$) during the pulse interval ($i_s$) between successive control pulses ($I_1$), and said method further comprising:

supplying the magnetization pulses ($I_2$) periodically at a pulse repetition rate synchronous to the repetition rate of said control pulses ($I_1$).

3. Method according to claim 2, characterized in that the magnetization pulses ($I_2$) are supplied with the same pulse repetition rate as the control pulses ($I_1$).

4. Method according to claim 1, characterized in that the magnetization pulses ($I_2$) are rectangular pulses.

5. Method according to claim 1, wherein a plurality of the flux pickups each includes ferromagnetic material with an electric winding (16), said magnetization step comprising supplying the magnetization pulse as an electric current pulse ($I_2$) to the electric winding (16) of each flux pickup;

said method further comprising:

continuously supplying a direct current ($I_4$) of identical magnitude and polarity to the electric winding (16) of each flux pickup so as to prevent a field reversal at the Hall generators during the field flux measuring step.

6. Method according to claim 1, characterized in that the method is employed (FIG. 1) for detecting the motion of the lower jaw of a human being.

7. A device for practicing the method according to claim 6, characterized in that two flux pickup blocks (6, 7) are symmetrically secured to a frame (5) arranged at a fixed relationship to a patient's head (1), four respective flux pickups (I through VIII) being arranged on each of said flux pickup blocks (6, 7).

* * * * *